(12) United States Patent
Wang

(10) Patent No.: US 8,278,315 B2
(45) Date of Patent: Oct. 2, 2012

(54) RADIOTHERAPY METHOD USING X-RAYS

(76) Inventor: Chia-Gee Wang, Millwood, NY (US)

( * ) Notice: Subject to any disclaimer, the term of this patent is extended or adjusted under 35 U.S.C. 154(b) by 2048 days.

(21) Appl. No.: 10/651,305

(22) Filed: Aug. 28, 2003

(65) Prior Publication Data

US 2005/0080019 A1    Apr. 14, 2005

Related U.S. Application Data

(60) Provisional application No. 60/408,358, filed on Sep. 5, 2002.

(51) Int. Cl.
*A61K 31/506* (2006.01)
*A61K 31/35* (2006.01)
*A61K 33/24* (2006.01)
*A61K 31/282* (2006.01)

(52) U.S. Cl. .................. 514/274; 514/460; 424/649

(58) Field of Classification Search .............. 514/274, 514/460; 424/649
See application file for complete search history.

(56) References Cited

U.S. PATENT DOCUMENTS

| | | | |
|---|---|---|---|
| 5,044,001 A | 8/1991 | Wang | 378/43 |
| 5,627,871 A | 5/1997 | Wang | 378/121 |
| 5,641,764 A | 6/1997 | Martin et al. | 514/80 |
| 5,859,065 A | 1/1999 | Brandes | 514/651 |
| 6,224,848 B1 | 5/2001 | Mills | 424/1.65 |
| 6,366,801 B1 | 4/2002 | Cash, Jr. et al. | 600/431 |

OTHER PUBLICATIONS

Goldman et al., Ed., Cecil Textbook of Medicine, 21st Edition, vol. 1, 2000, pp. 1060-1074.*
Larson, D. et al. "Auger Electron Contribution to Bromodeoxyuridine Cellular Radiosensitization." *International Journal of Radiation Oncology •Biology• Physics*, (1989) 16(1), pp. 171-176.
Oxford Instruments Technical Data Sheets. "UltraBright: Microfocus X-Ray Source." X-Ray Technologies, Inc.
Mills, Randell L. et al. "A novel cancer therapy using a Mössbauer-isotope compound." *Nature*, (1988) vol. 336, pp. 787-789.
Laster, B.H. et al. "Photon Activation of Iododeoxyuridine: Biological Efficacy of Auger Electrons." *Radiation Research: An International Journal*, (1993) 133, pp. 219-224.

* cited by examiner

*Primary Examiner* — James D Anderson
*Assistant Examiner* — Gregg Polansky
(74) *Attorney, Agent, or Firm* — Ladas & Parry LLP

(57) ABSTRACT

A method of treating living mammals including humans uses x-rays to disrupt DNA in malfunctioning cells such as cancerous or tumorous cells. A compound comprising a pre-selected element is administered to the mammal so that the compound associates with DNA. Then a localized region of cells which contains the malfunctioning cells is irradiated with line emission x-rays of an energy selected to cause emission of Auger electrons from the pre-selected element of the compound to disrupt DNA proximate to the irradiated pre-selected element. A kit useful for the treatment comprises an x-ray tube capable of emitting monochromatic line emission x-rays and a compound which associates with DNA and has an element which when irradiated emits said Auger electrons.

94 Claims, 6 Drawing Sheets

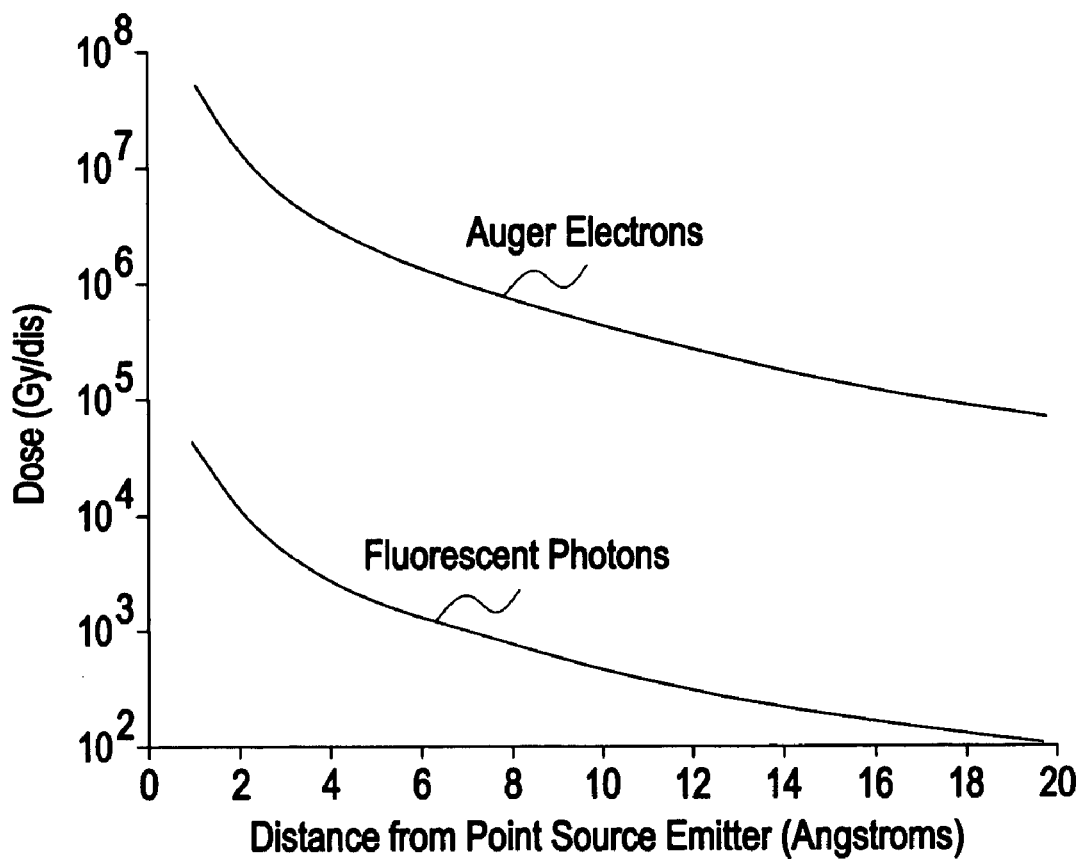

Tungsten target
A — 20 kV
B — 15 kV
C — 10 kV
D — 15 kV
E — 40 kV
F — 50 kV

160 KVp Tungsten Spectra

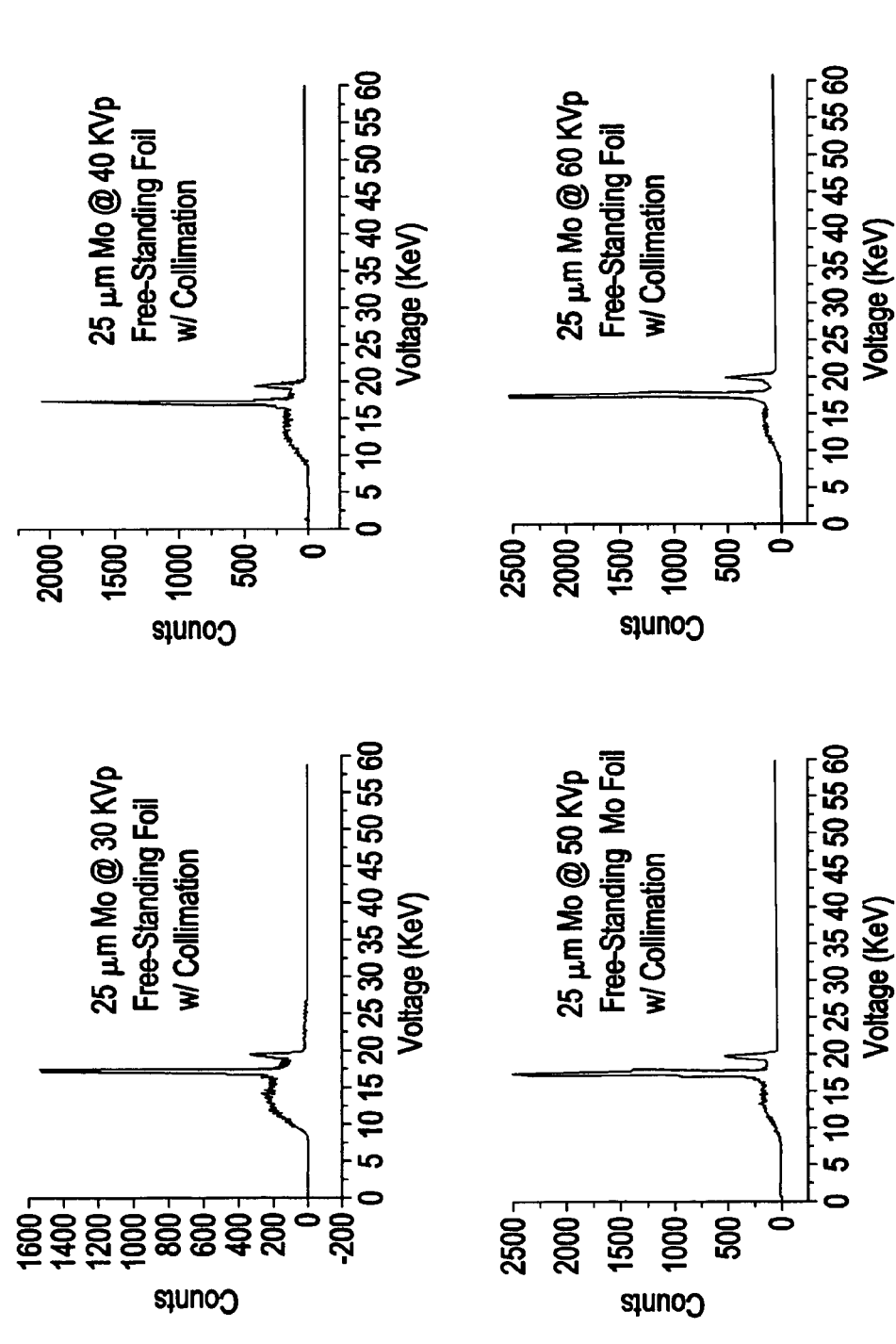

The Emission Spectrum of an End-Window Ag Target

RADIOTHERAPY METHOD USING X-RAYS

CROSS-REFERENCES TO RELATED APPLICATIONS

This application claims the benefit of U.S. Provisional Application No. 60/408,358, filed Sep. 5, 2002.

BACKGROUND OF THE INVENTION

1. Field of the Invention

The present invention relates to a method of treating malfunctioning cells in living mammals, including humans, in which x-rays are used to disrupt DNA in the malfunctioning cells; to a kit useful for such treating; and to compounds, complexes and compositions useful for such treating. More particularly, the invention relates to treating cancerous and tumorous cells in humans, using line emission x-rays to generate ionizing radiation from an element carried by a compound into proximity to the DNA of target cells.

2. Description of the Related Art

In the United States, there are two million new cancer cases each year. About 600,000 patients undergo radiation therapy and almost two million undergo chemotherapy at a cost of well over $100 billion. Both of these therapeutic approaches rely on the increased sensitivity of rapidly dividing cancerous cells to toxic agents. Since the toxic agent is often supplied to the whole body and many normal body tissues are also dividing rapidly (hair roots, cells of the gut lining, etc.) a balance must be achieved between killing the maximum number of cancerous cells while doing the minimum damage to normal body cells. Considerable effort has been made either to maximize this discrimination or to target the toxic agent specifically to the tumor cells. The approach of the invention is designed to overcome the drawbacks inherent in radio- and chemotherapy by using localized delivery of x-rays to activate elements that generate ionizing radiation which will damage cellular DNA. Compounds comprising such elements can be given to the whole body and only activated in the region of the tumor by a narrow, focused beam of specific energy x-rays.

Efforts to selectively target cancer cells are disclosed in prior art such as U.S. Pat. No. 5,859,065 which discloses improved therapy by first treating the subject with a compound that inhibits normal cell proliferation while promoting malignant cell proliferation, and then treating with a chemotherapeutic agent; and in U.S. Pat. No. 6,366,801 which discloses using compounds having heavy elements to enhance the radiotherapy dose ratio of tumor dose to normal tissue dose. A ratio of up to 10:1 is claimed to be achieved.

U.S. Pat. No. 5,641,764 discloses using halogenated DNA ligands to induce radiation damage in DNA in response to ionizing or ultraviolet (UV) radiation. An iodinated ligand was found to sensitize cell destruction by UV exposure, and the inventors speculate that the ligands may also act as sensitizers of ionizing radiation (from radioactive nuclei or from x-rays).

U.S. Pat. No. 6,224,848 discloses a method of cancer therapy. A compound which binds to target tissue and contains a gamma radiation absorber isotope is administered. The bound compound is excited by an apparatus using a radiation source consisting of a radioactive isotope or a synchrotron, to release resonant gamma radiation. The gamma radiation is converted internally by the isotope at the target tissue into particle radiation followed by an Auger cascade which is said to damage DNA. Disadvantages of use of a synchrotron source are discussed hereinafter in a section headed "Functional X-Rays".

An x-ray apparatus in which an e-beam is generated in a tubular chamber and focused on a thin metal foil supported inside the chamber on an end window transparent to x-rays is described in the present applicant's U.S. Pat. No. 5,044,001, the disclosure of which is incorporated herein by reference.

A compact end window, transmission x-ray tube assembly suitable for use in the present invention is disclosed in the present applicant's U.S. Pat. No. 5,627,871, the disclosure of which is incorporated herein by reference. In this x-ray tube, the composition of a thin metal foil target and the energy of an e-beam are selected to generate a microfocused bright beam of x-rays of a pre-selected energy.

SUMMARY OF THE INVENTION

The method of the invention utilizes the emission of Auger electrons from elements, particularly heavy elements, that have been irradiated with x-rays, particularly monoenergetic x-rays tuned to the K-absorption edge of the element. These electrons can deliver concentrated dosages of ionizing radiation of more than $10^6$ gray (Gy) per activation to localized areas only a few atomic diameters across. By "activation" is meant each separate irradiation when more than one is done. In practice, the element which can emit ionizing radiation is coupled to a carrier compound which enters the cells and intercalates into or binds with DNA, so that irradiation of the emitter element will release Auger electrons resulting in damage to crucial cellular components. Compounds which are substantially non-toxic are advantageous since they can be administered throughout the body, without needing to be selective for, or having an affinity to, specific organs or tissues. The substantially non-toxic compounds can be given at whole body dosages and will not be activated until illuminated with x-rays of the appropriate energies. The term "whole body dosage" herein means a dosage which may be distributed through the body and may be given up to the maximum dosage tolerated, i.e. without causing unacceptable toxicity or collateral damage to non-cancerous tissue. The x-ray beam provides the ability to localize the release of Auger electrons to eliminate cancerous, tumorous or malfunctioning cells with minimum damage to other normal body tissues. A number of compounds meet the necessary criteria for low or no toxicity and for intercalating or binding to DNA, and are available coupled to suitable elements including heavy elements such as iodine. Compounds having higher toxicity also may be used, e.g. at lower dosages or when the compounds have an affinity for cancerous tissue.

According to the invention there is provided a method for treating malfunctioning cells in a living mammal, which comprises:
  (a) administering a compound which associates with DNA in cells of said mammal, said compound comprising a pre-selected element; and then
  (b) irradiating a selected region, in which malfunctioning cells having said compound associated with DNA are located, with line emission x-rays of an energy selected to cause emission of Auger electrons from said pre-selected element of said compound in a dose effective to disrupt DNA proximate to the irradiated pre-selected element.

Also according to the invention there is provided a method of treating tumors or cancer in a human in need of such treatment, which comprises:

(a) administering to the human a compound which associates with DNA in cells of said human, said compound comprising a pre-selected element; and then
(b) irradiating a selected region, in which cancerous cells having said compound associated with DNA are located, with line emission x-rays of an energy selected to cause emission of Auger electrons from said pre-selected element of said compound in a dose effective to disrupt DNA proximate to the pre-selected element.

Still further provided according to the invention is a method of treating cancer in a human in need of such treatment, which comprises:
(a) administering to the human a compound which associates with DNA, in cells of said human, said compound comprising a pre-selected element selected from the group consisting of Br, Ru, I, Gd and Pt; and then
(b) irradiating at least once, by means of an end window transmission x-ray tube, a selected region, in which cancerous cells having said compound associated with DNA are located, with line emission x-rays of an energy selected to cause emission of Auger electrons from said pre-selected element of said compound in a dose effective to disrupt DNA proximate to the irradiated pre-selected element, said dose for each activation of said x-ray tube being at least about $10^6$ Gy within a distance from the pre-selected element of the compound of up to about 10 angstroms.

Also further provided according to the invention is a kit for treating malfunctioning cells in a living mammal, which comprises:
(1) an x-ray tube having a target comprising a selected metal, said tube being capable of emitting monochromatic line emission x-rays; and
(2) a compound comprising a selected element, said compound being capable, upon administration to said mammal, of associating with DNA in cells of said mammal;
the selected metal of said target and the selected element of said compound being selected together: (a) for said metal of said target to emit line emission x-rays having an energy above and near the K-absorption edge or the L-absorption edge of the selected element of said compound, and (b) for said element of said compound to release a dose of Auger electrons upon irradiation by said line emission x-rays.

BRIEF DESCRIPTION OF THE DRAWINGS

FIG. 2 is a graphical illustration of the relation between the dose of emitted radiation and the distance from the emitter.

FIG. 4a depicts graphical spectra of radiation emitted from an end-window x-ray tube with a Mo target at different e-beam energies delivered to the target.

DETAILED DESCRIPTION OF THE INVENTION

Figure 1:
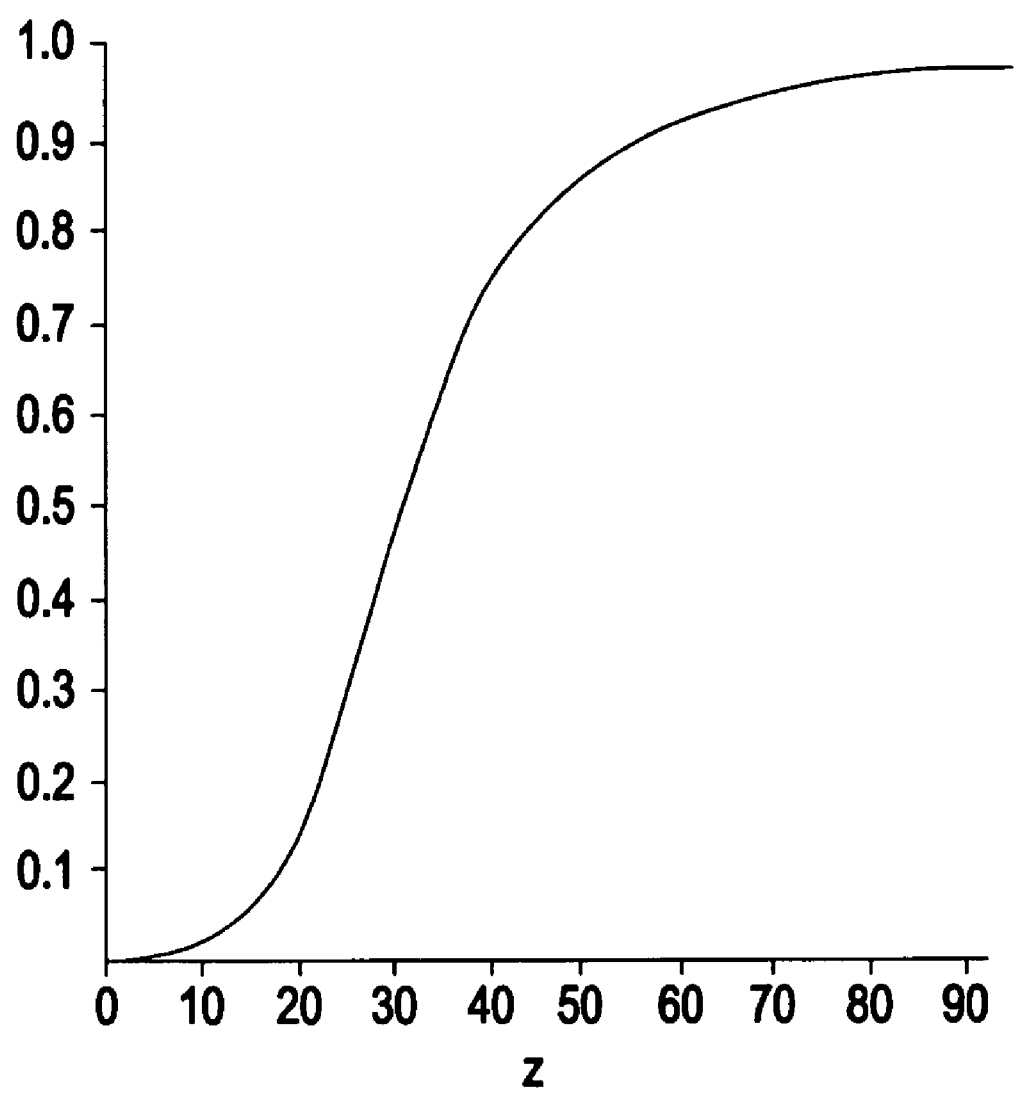
FIG. 1 is a graphical illustration of the relation between the fraction of energy emitted as fluorescent photons upon inner shell ionization and atomic number.

The key component of the method of the invention is the ability to produce bright x-ray beams of defined line emissions. Traditionally, this could be done using synchrotron radiation but in this case, the brightness of the photon flux drops by $E^{-4}$ (where E is the photon beam energy) and as a result is virtually useless at x-ray photon energies greater than 20 kV, well below the energy needed for the heavy element triggers to be used. X-ray tubes, in contrast, provide a photon flux that increases by $E^{1.7}$ with increasing electron beam energy. But traditional x-ray tubes produce largely Bremsstrahlung or slow-down radiation, and do not provide the required specific line emissions. In the present invention, a linear x-ray tube is used which produces largely line emissions where the energy of the emission lines can be selected by selecting the metal element used for the target. Appropriate targets can then be used to give x-ray line emissions tuned to the absorption edge of the elements which will emit Auger electrons.

Chemotherapy is well known for its side effects, and a great deal of effort has been spent to reduce the side effects of the whole body treatment. Radiation therapy, on the other hand, can deliver topical treatment, but the treatment is generally not sensitive to the metabolic uptake of the targeted tissues. If the topical delivery of radiation can be combined with the cellular uptake of therapeutic agents, it brings about indeed a powerful tool for cancer treatment. Herein, this therapy uses a novel tool, a "functional x-ray", where x-rays with monochromatic line-emissions are used to trigger the emission of Auger electrons in situ. These low energy Auger electrons with their total ionization energy transferred within a few atomic distances, provide a dose at $10^6$ Gy or higher, and thereby produce the desired disruption of DNA in situ.

The therapeutic effect will be delivered directly to the targeted DNA, at the targeted tumor-bearing site. The aim is to drastically reduce the exposure of toxicity to the body's healthy organs or tissues.

In the method of the invention, a compound comprising a pre-selected element is administered to a mammal, for example a human, having malfunctioning cells. The compound may be administered to the mammal for treatment of the mammal or for a treatment of tissues or organs removed from the mammal. Administering the compound also is meant to include administering it directly to tissues or organs removed from the mammal. Malfunctioning cells include cancerous or tumorous cells; and otherwise defective cells when such defective cells may be locally segregated such as pre-cancerous cells, polyps, and the like. "Malfunctioning" is broadly meant to include cells having abnormal DNA and cells producing an abnormal quantity or quality of cellular products. Tissues or organs removed from the body may be removed for purposes such as transplanting, e.g. bone marrow, or for treatment outside the body of the mammal and subsequent return to the body.

The administered compound associates with DNA for example by intercalating into the DNA helix or by binding to the DNA. The compound may have an affinity for both normal and malfunctioning cells. Therefore, it is preferred for the compound to be substantially non-toxic. By "substantially non-toxic" it is meant that the administered compound does not cause harmful or life-threatening damage to normal tissue and organs of the mammal in doses effective for accomplishing the irradiation step of the method of the invention. The use of compounds which are substantially non-toxic facilitates administration of a whole body dose of the compound. Administration of a whole body dose without serious effect on normal tissue is especially advantageous due to reducing or avoiding side-effects and enabling simple means of administration.

However, compounds which have some toxic effect, e.g. chemotherapeutic compounds, and which associate with DNA also may be used. In using such compounds it is preferred that they have a selective affinity for malfunctioning cells, i.e. that such compounds be taken up more by malfunctioning or cancerous cells, or organs comprising malfunctioning or cancerous cells, than by normal cells or organs. Another way of using compounds having a toxic effect is by direct application to the tissue to be treated, and carrying out the irradiation step soon after application. Alternatively, compounds which have more of a toxic effect may be used in a dosage which is low enough to avoid serious side effects, but is sufficient to accomplish the irradiation step of the invention.

Examples of a suitable compound are annamycin (ANN), bromodeoxyuridine (BrdU), bromodeoxycytosine (BrdC), iododeoxyuridine (IdU), and cisplatin.

The element, i.e. pre-selected element, of the compound is an element which will emit Auger electrons in a dose effective to damage or disrupt closely adjacent DNA upon being irradiated by line emission x-rays of an energy selected to cause the emission of Auger electrons from the pre-selected element.

Preferably, the pre-selected element of the compound will have an atomic number (Z) in the range of from 35 to 79. More preferably, Z will be from 44 to 78. In this range, preferred elements are the heavy elements Ru, I, Gd and Pt. Lighter elements such as bromine may be used for some treatments. The use of lighter elements, however, is limited as more fully described below because the line emission x-ray energy needed to trigger the emission of Auger electrons is relatively low compared to the energy required for the heavy elements. As a result of the lower energy used, tissue penetration by the line emission x-rays is low. Consequently, lighter elements such as Br may be used for treatments where the malfunctioning cells of the mammal's body are superficial, for instance, in treatment of melanoma.

To minimize any potential toxic effects from the administration of the compound, preferably the compound is selected to have a high rate of excretion by normal physiological processes. For the same reason, it is preferred that the compound should be selected for stability against dissociation of the pre-selected element from the compound during the time prior to substantially complete excretion or metabolism of the compound.

The compound may be administered in any way that is effective for bringing the compound into contact with malfunctioning cells. In most cases administration will be done intravenously. Depending on the properties of the compound, oral administration may be used. In addition, administration can be selectively directed to specific organs or tissues containing malfunctioning cells, e.g. by direct injection or by selecting compounds having an affinity to the cells, organs or tissues to be treated. The dose of the compound is dependent on the mammal being treated and on the compound being used. In most instances, a whole body dose can be administered in an amount effective to bring the compound into close relationship with DNA in malfunctioning cells, such dose being substantially non-toxic to the normal cells.

As discussed more fully hereinbelow, the line emission x-rays required in the method of the present invention preferably are generated by use of an end window transmission x-ray tube which can produce bright line emission x-rays. A preferred x-ray tube employs an e-beam in the tube which is focused on a thin target having a thickness of up to about 40 µm, said target being inside the tube and coated on or functioning as part of the end window. Both the target and the e-beam energy are selected to provide substantially monochromatic line emission x-rays having an energy above and near the K-absorption edge or the L-absorption edge of the pre-selected element of the compound. Preferably, the thin target is selected from the elements Rb, Mo, Ag, La, Sr and Tm.

By selection of the pre-selected element of the compound and the characteristics of the x-ray tube, a specific energy of line emission x-rays can be selectively employed to result in irradiation of the pre-selected element causing Auger electrons to be released with a dose of at least about $10^6$ Gy. This dose is most effectively released within a distance from the pre-selected element of the compound of up to about 10 angstroms.

The irradiation step, i.e. activation, of the pre-selected element to cause release of Auger electrons may be done only once for effective treatment. The activation can, however, be repeated one or more times. In the first activation as well as in each repeated activation, a dose of at least about $10^6$ Gy may be released.

In the method of the invention, the irradiation provided by line emission x-rays is directed to a localized region of cells which contains or which predominantly contains malfunctioning cells, to localize the effect of disrupting DNA to the malfunctioning cells and minimize the effect on normal cells.

The irradiation may be directed by CT or MRI image guided delivery systems, which are well known for radiotherapy.

The Generation of Auger Electrons

When an atom undergoes an inner shell ionization, either by scattering with a photon or electron, or by a K-capture where a proton from the nucleus captures a K-electron and forms a neutron, which reduces the number of charges Z in the nucleus by one unit and the atom becomes a (Z minus 1) chemical element, the atom undergoes either a fluorescence or a radiationless transition. All x-rays, fluorescent or otherwise, deliver their ionizing radiation in the tissue initially through the generation of photons and electrons. FIG. 1 shows the fluorescence yield, as a fraction of the total yield plotted against Z. It can be seen that the fluorescence yield when Z is the atomic number for iodine is 90%, for Br is 62%, and for Ti is 20%. The radiationless transition involves for example the L-electron dropping to K, but the transition energy being absorbed by another L-electron which uses it to leave the atom, thus creating two L-shell ionizations, which in turn, allows two M-electrons to drop to the L-shell, and the transition energies being used to allow two M-electrons to leave the atom, creating 4 M-shell ionizations, etc. In short, the radiationless transition, the "Auger series" or "Auger cascade", produces a string of soft ionizing electrons typically at 14-18 eV each, all initiated from a single inner shell (mostly K) ionization. For light atoms such as titanium, the Auger yield (at 80% as against the fluorescence yield at 20%) is very high, but each Auger cascade would produce only a few electrons, whereas heavy atoms such as iodine, have only a 10% Auger yield, but produce many more Auger electrons per each event, the total Auger doses being approximately of the same order of magnitude for these two elements.

Table 1 provides a detailed calculation of the titanium transition states, with each possible transition probability included. FIG. 2 illustrates the radiation dose (in water) of Auger electrons as well as the total photon dose. For titanium, Z is low and the photons are relatively soft, yet the electron dose is already more than 3 orders of magnitude higher than the photon dose at small distances. For iodine, the fluorescent photons at 30 kV are much harder, yielding a much smaller LET (linear energy transfer), thus giving rise to a higher electron/photon dose ratio even though the fluorescent yield for iodine is 90%, as shown in FIG. 1.

TABLE 1

| Properties | Element | |
|---|---|---|
| | Titanium | Calcium |
| Atomic Number (Z) | 22 | 20 |
| K-shell Energy (keV) | 4.966 | 4.038 |
| Fluorescent, Auger Yield | 0.22, 0.78 | 0.16, 0.84 |
| Energy, Range of Primary Auger | ≈16 eV, 9 Å | ≈16 eV, 9 Å |

| The Predicted Auger for Titanium | | | |
|---|---|---|---|
| Transition | Probability | Energy (keV) | Range (Å) |
| X-rays | | | |
| K-Shell | 0.22 | 4.96 | ≈1 × 10$^6$ |
| Auger Electrons | | | |
| KL$_1$L$_1$ | 0.004 | 4.17 | 6190 |
| KL$_1$L$_2$ | 0.017 | 4.26 | 6410 |
| KL$_1$L$_3$ | 0.004 | 4.29 | 6500 |
| KL$_2$L$_2$ | 0.005 | 4.36 | 6670 |
| KL$_2$L$_3$ | 0.047 | 4.38 | 6720 |
| KL$_3$L$_3$ | 0.004 | 4.40 | 6760 |
| KL$_1$X | 0.005 | 4.80 | 7810 |
| KL$_2$X | 0.004 | 4.90 | 8100 |
| KL$_3$X | 0.007 | 4.91 | 8120 |
| KXY | 0.001 | 5.39 | 9470 |
| L$_1$MM | 0.002 | 0.60 | 335 |
| L$_2$MM | 0.038 | 0.49 | 259 |
| L$_3$MM | 0.179 | 0.48 | 253 |
| MXY | 0.463 | 0.016 | 8.9 |

An investigation of a method called "nuclear chemotherapy" was done many years previously at Sloan-Kettering Research Institute in New York, by Dr. Chia-Gee Wang and Dr. Lawrence Helson. The research was done using $^{77}$BrdC, where $^{77}$Br (half-life at 57 hours) would undergo a K-capture and deliver 10$^6$ or more Gy at a small distance. The oxidation of BrdC to BrdU can be blocked by the non-toxic H$_4$U and therefore excluding BrdC from being incorporated into the DNA pool. Certain transformed cells, on the other hand, would make use of a more primitive kinase to bypass the H$_4$U blockage, and incorporate BrdC to form BrdU. The $^{77}$Br was made by adding an a particle to $^{75}$As in a facility in the U.K. $^{77}$Br was obtained in liquid solution, and $^{77}$BrdC was made. Of the ten neuroblastoma lines tested, two of the ten lines were sensitive to such an attack. Treating the sensitive tumor lines, in fact, does not cause the cell death immediately. The cells simply stopped mitosis while continuing most of the cellular functions. The Auger electrons from the $^{77}$BrdU delivered such a high dose of the DNA duplex that no cellular repair was possible. This shows that the high ionizing dose is exceedingly localized, and would not harm the cell if the BrdC molecule is not incorporated into the DNA pool, as evidenced by the 8 non-sensitive lines of the 10 neuroblastoma lines to which $^{77}$BrdC was administered, and some doses of the $^{77}$BrdC were at a level a few orders of magnitude higher than those used for sensitive lines.

The inner shell ionization of Br can be initiated by a K-capture or by a photon with energy just above the K-absorption edge of Br at 13.475 kV where the photoscattering cross section jumps by an order of magnitude. Such photon can be the Kα1 of Sr at 14.164 kV. But the Br photons are too soft for other than surface-located tissue; they cannot penetrate various parts of the body tissue. They can be used for superficially located tumors. In the method of the invention, therefore, heavier elements are generally preferred, with harder photons. Iodine, with its K-edge at 33.164 keV, would require much harder line-emission (from the Kα1 of La at 33.440 kV) to trigger its Auger emissions. Table 2 shows the energies of x-ray tube target elements in relation to the K-absorption energies of elements used to emit Auger electrons.

TABLE 2

| Energies For Auger Generating Element and X-ray Tube Target | | | |
|---|---|---|---|
| Auger Element | K-absorption edge (ev) | X-ray Target | Emission Line (ev) |
| Calcium Ca | 4,038 | Scandium Sc | 4,090 (Kα$^1$) |
| | | | 4,085 (Kα$^2$) |
| Titanium Ti | 4,964 | Chromium Cr | 5,414 (Kα$^1$) |
| | | | 5,405 (Kα$^2$) |
| Bromine Br | 13,475 | Strontium Sr | 14,164 (Kα$^1$) |
| | | | 14,097 (Kα$^2$) |
| Iodine I | 33,164 | Lanthanum La | 33,440 (Kα$^1$) |
| Gadolium Gd | 50,229 | Thulium Tm | 50,730 (Kα$^1$) |
| Yttrium Y | 17,037 | Molybdenum Mo | 17,478 (Kα$^1$) |
| | | | 17,373 (Kα$^2$) |
| Ruthenium Ru | 22,118 | Silver Ag | 22,162 (Kα$^1$) |

It has been found that Auger electrons will damage the DNA duplex beyond repair while remaining harmless in the cytoplasm. Gd has a K-edge of 50.229 kV and can readily be excited by Kα1 of Tm at 50.730 kV. As seen from FIG. 2, more than 10$^6$ Gy can be delivered by the Auger electrons up to a distance of 10 Å.

The Functional X-Rays

Figure 3A:
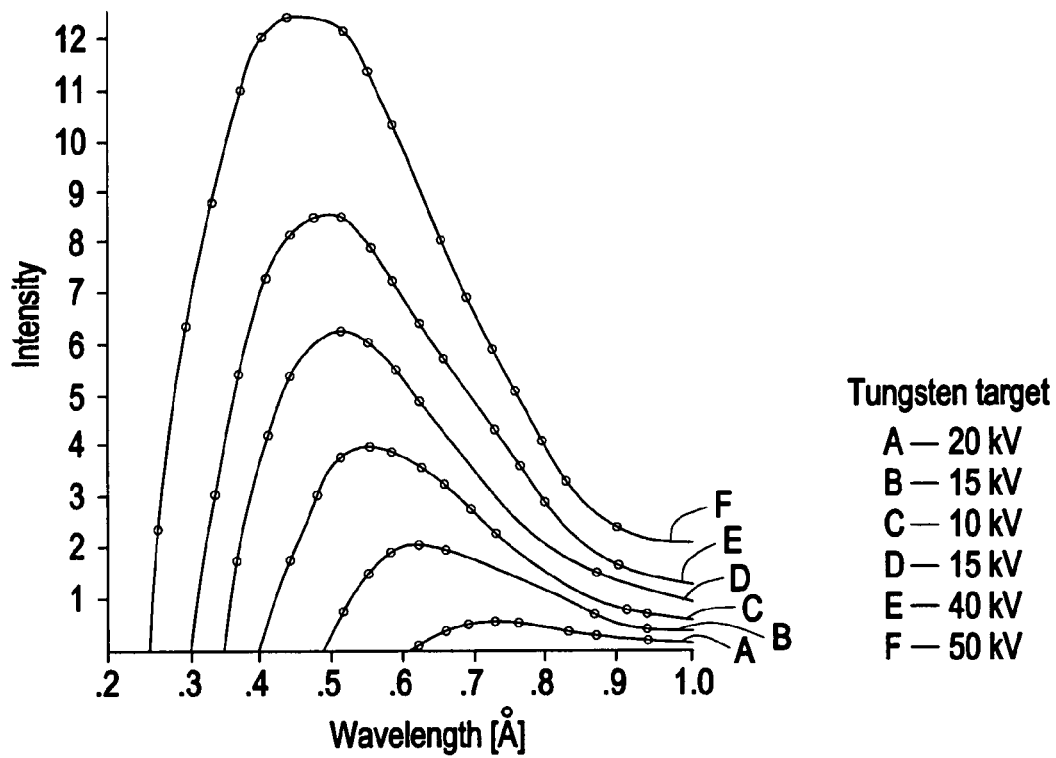
FIG. 3a is a graphical illustration of the spectrum of bremsstrahlung radiation.
Figure 3B:
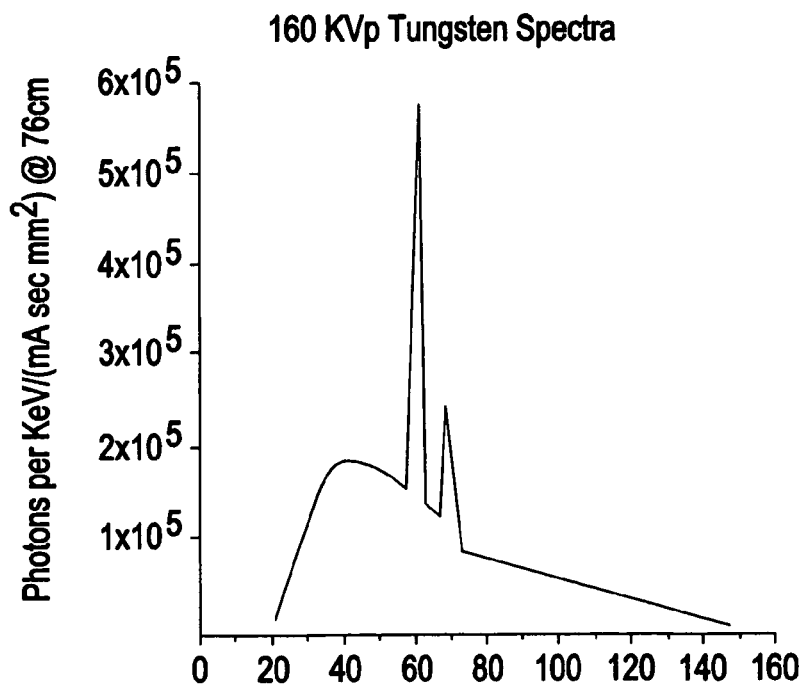
FIG. 3b is a graphical illustration of the spectrum of radiation emitted from a conventional side-window x-ray tube.

X-rays can be produced by synchrotron radiation or by an x-ray tube. The photon flux of a synchrotron drops by $E_p^{-4}$, with $E_p$ the photon energy, and renders the synchrotron ring useless for photon energies greater than 20 kV. X-ray tubes, on the other hand, become brighter as the photon flux $\sim E_e^{1.7}$, with $E_e$ the peak e-beam energy of the tube. Conventional x-ray tubes deliver x-rays with bremsstrahlung ("brem") which is the German word for "slow-down radiation". Brem basically have a continuum spectrum, as shown in FIG. 3a. Conventional x-rays are emitted at ~90° from the e-beam path, with higher voltage delivering harder photons and brighter flux. FIG. 3b shows the spectrum of a typical modern x-ray tube with high voltage e-beam and a solid tungsten target. The width of the tungsten line-emissions Kα and Kβ, is the width of the detector resolution. A high resolution detector can reduce the line width by a factor of ten or more.

The x-ray photons from the conventional side-window x-ray tube can be used for imaging, or for radiation therapy, but they are not useful for the method of the present invention which requires delivery of line emission x-rays of a pre-selected energy.

Localized x-ray irradiation of elements, particularly heavy elements, in accordance with the invention may be done, for example, using an x-ray tube with an end-window target as described in above-mentioned U.S. Pat. No. 5,627,871. The tube is available from the assignee of the present applicant, NanoDynamics, Inc., 510 East 73$^{rd}$ Street, New York, N.Y.

Figure 4B:
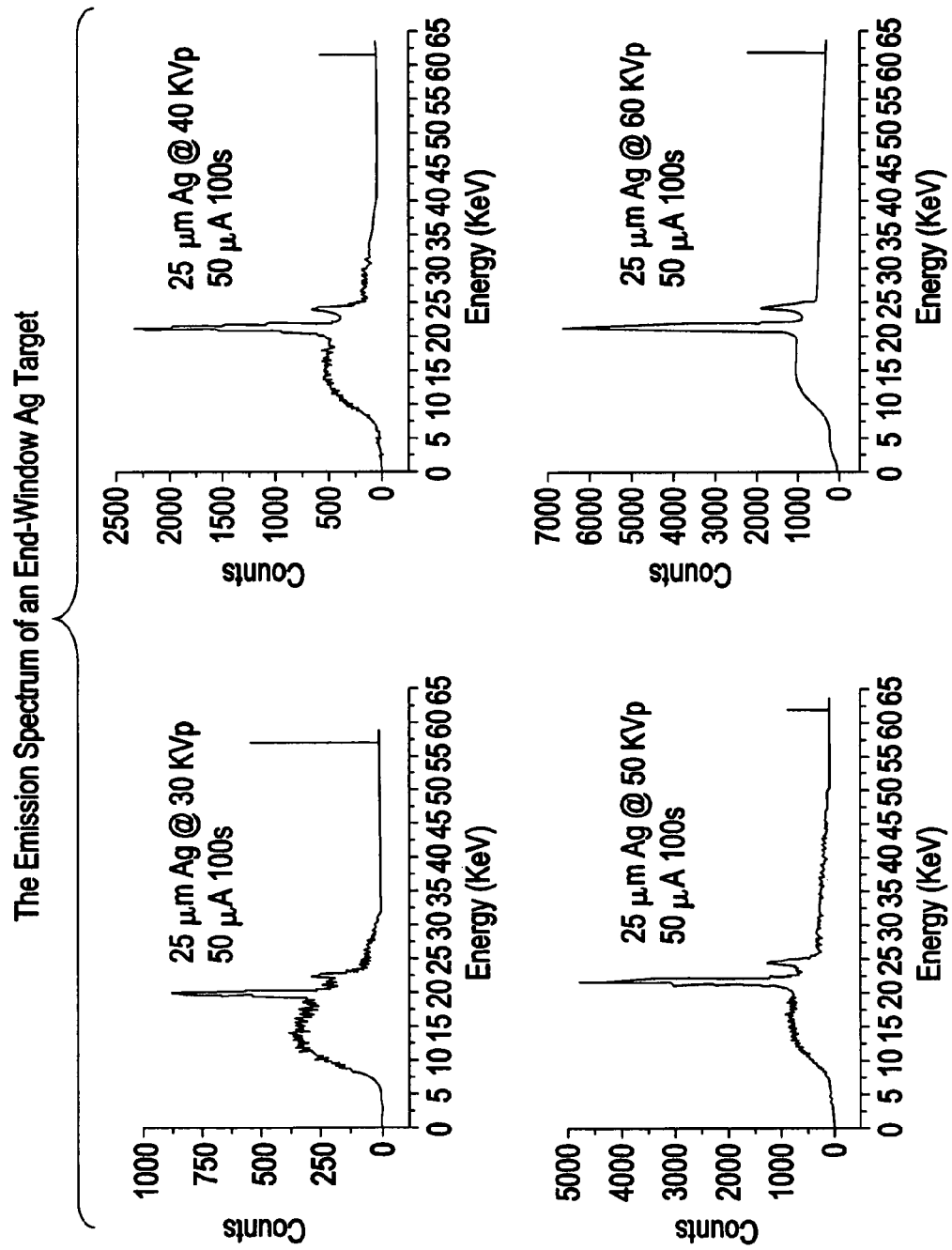
FIG. 4b depicts graphical spectra of radiation emitted from an end-window x-ray tube with a Ag target at different e-beam energies delivered to the target.
Figure 5:
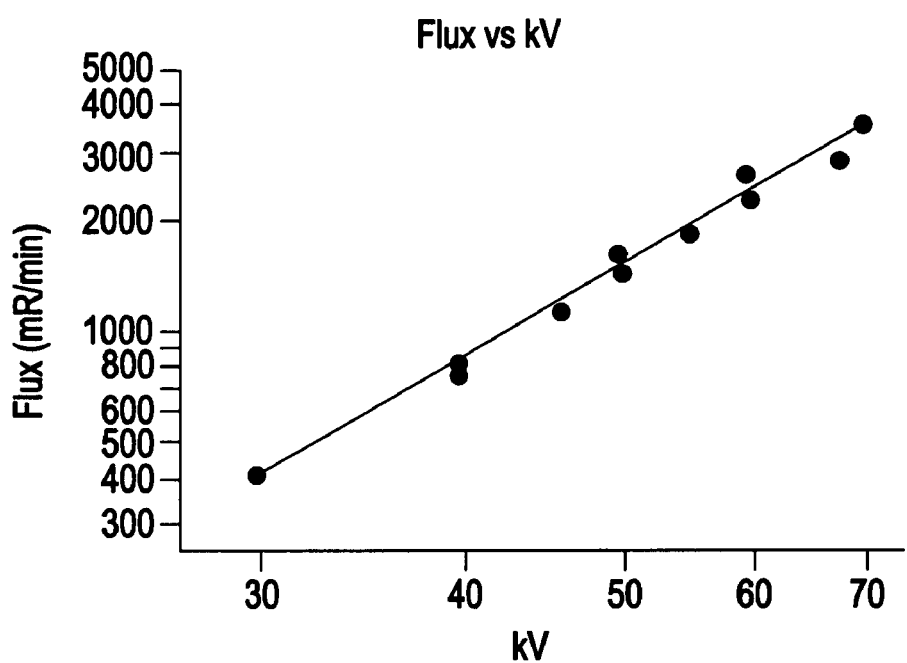
FIG. 5 is a graphical illustration of the relation between radiation flux and e-beam voltage for an end-window transmission x-ray tube.

[0021] In use of this tube, the x-ray flux is delivered along the e-beam path and transmitted through the end-window. The x-ray target material is coated on a beryllium end-window which keeps the vacuum seal, conducts the current and the thermal load, and maintains the x-ray focal spot at a distance of only a fraction of one mm from the outside, or from the subject to be irradiated, if necessary. The e-beam is microfocused on the transmission target, which is coated with a typical thickness of 10-20 μm. Electrons are stopped by the target metal within the first few microns or so, and the remaining target thickness functions as a filter, transforming the high energy beams to fluorescent line-emissions characteristic of the target element. FIG. 4a shows the emission spectrum of an end-window molybdenum target and FIG. 4b shows the spectrum of an end-window silver target. It is of interest to note that as the e-beam energy varies from 30 kV to 60 kV, the emission spectrum simply becomes "cleaner and purer", with mainly the fluorescent K-emissions of the target. A careful examination of the spectra shown in FIGS. 4a and 4b indicates that most of the x-ray flux is concentrated in the line-emissions. These emissions can be used for the functional irradiation to excite the compounded element from which the induced Augers will cause the desired DNA disruption. Also, the end-window target design not only provides a photon flux with a mostly monochromatic spectrum, but the total x-ray flux is also much brighter than with conventional tubes. FIG. 5 shows the flux versus applied voltage, or flux $\sim E_e^{2.5}$ as compared to the conventional tube brightness with flux $\sim E_e^{1.7}$ This added brightness is due to the fact that the transmission target design can take advantage of making use of the radiation along the e-beam path, which is favored by the forward relativistic transform of the dipole radiation at higher e-beam energies. This forward radiation is buried in the solid target in a conventional x-ray tube.

Figure 6:
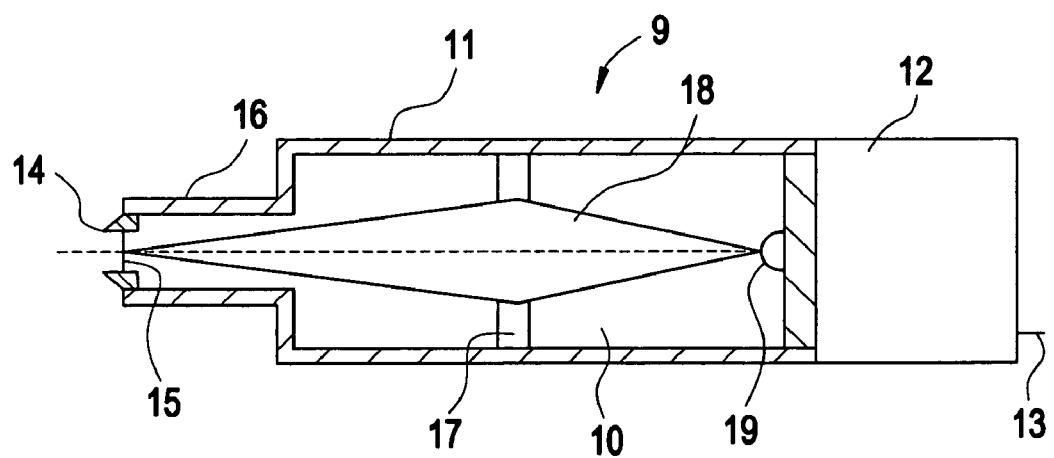
FIG. 6 is a schematic elevational view partly in cross-section of a compact end-window transmission x-ray tube useful in the present invention, taken from the above-mentioned U.S. Pat. No. 5,627,871.

FIG. 6 illustrates the above-mentioned end window x-ray tube integrated with a high voltage power supply. In FIG. 6, x-ray tube 9 comprises an evacuated tubular chamber 10 enclosed by a tubular ceramic envelope 11. At one end chamber 10 is connected to end window 14. At its other end, chamber 10 is connected to a power supply 12 which is connected by line 13 to an electrical current supply, not shown, such as a 120 V AC outlet. The power supply may be adjusted so that the energy of x-ray photons from the tube ranges up to 100 KV. Power supply 12 comprises transformers and circuit elements for supplying current to an emitter 19 and to electrostatic lens 17. The components of power supply 12 are contained in a housing which may be made of plastic or metal, and said housing may be filled with an insulating oil or gel.

End window 14 has on its inside surface a metal foil target 15. The end window may be mounted in a tubular extension 16 of smaller diameter than ceramic envelope 11. Tubular extension 16 may be ceramic or metal, is usually stainless steel and, being open to the interior of chamber 10, is evacuated. A typical outside diameter of tubular extension 16 is ⅝ inch. Tubular extension 16 may be surrounded by an annular magnetic coil or lens (not shown). Within chamber 10 is at least one electrostatic lens 17 which focuses e-beam 18.

Contained in chamber 10 is e-beam emitter 19 connected to said power supply 12. The e-beam emitter 19 may comprise a whisker such as a whisker of a tungsten filament. The whisker may have a diameter of several microns and a chemically etched tip of submicron size, from which e-beam 19 is generated. The e-beam is focused by electrostatic focusing 17. Further focusing may be accomplished by the above-mentioned magnetic lens.

Because of the much higher quantum efficiency of producing x-rays along the e-beam path, a small power supply shown in FIG. 6 delivers an x-ray flux as bright as that of a typical mammography instrument, yet it has less than 1/10 of the weight and size.

Examples of Compounds Having An Affinity to DNA

One molecule which is a candidate for use in the method of the invention is the anti-cancer drug annamycin. Not only does this small antibiotic bind to DNA, but it contains one covalently linked heavy element, iodine.

The first anthracycline antibiotics were developed in the 1960's, and since that time, this class of molecule has been shown to exhibit an extremely wide spectrum of anti-neoplastic activity. Indeed, only a few cancer types (such as colon cancer) are refractory to this class of drug. The most extensively used anthracycline is doxorubicin (DOX) which is effective against most hematological malignancies and certain solid tumors, such as breast carcinoma or osteosarcoma.

Doxorubicin and annamycin have the following structures:

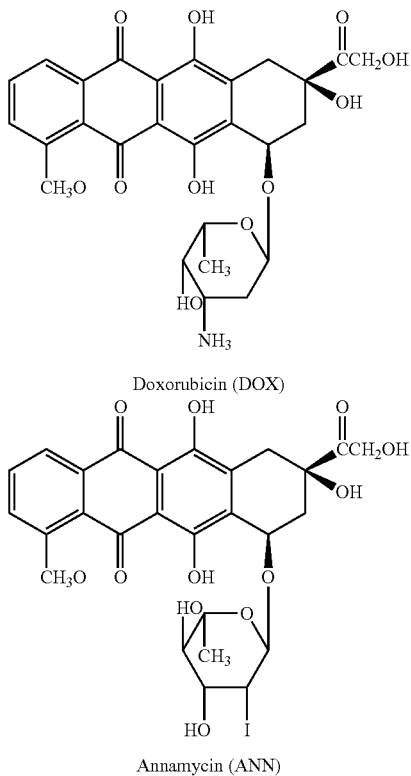

Doxorubicin (DOX)

Annamycin (ANN)

DOX, like all anthracyclines, intercalates into DNA, binding between adjacent base pairs. Its sugar moiety is an essential component of the class, as it interacts with the DNA minor groove. The anthracyclines induce a number of intracellular effects, and a variety of modes of action have been proposed to account for their anti-cancer activity. While cellular targets for anthracyclines include both nuclear and cytoplasmic components, the most dominant determinant is inhibition of topoisomerase II. Again, the sugar moiety is essential for anti-topo II activity. Nuclear topoisomerases play a major role in DNA metabolism by stimulating single (type I) or double (type II) strand breakage and rejoining along the DNA phosphodiester backbone. Topoisomerases function in DNA replication, recombination, transcription, chromosome segration, and the maintenance of chromosome structure. DOX exposure to sensitive cells, and subsequent topoisomerase I inhibition, leads to an accumulation of single-strand and double-strand DNA breaks, and eventual cell death. In addition to catalytic inhibition of the enzyme, DOX may function through stabilization of the DNA/topoisomerase II ternary complex.

While anthracycline-mediated topo II inhibition is generally agreed to be essential for cell death, additional cellular targets exist. Some anthracyclines target the regulatory domain of protein kinase C, a protein involved in signaling pathways via protein phosphorylation. In addition, anthracyclines stimulate hydroxyl free radicals, which may contribute to observed DNA-protein crosslinking in treated cells; it is possible that free radical formation may be cell or tissue specific.

While DOX has been extremely successful as a broad spectrum anti-cancer agent, serious side effects, and the development of drug resistance, continue to limit its use and efficacy. The major side effects of DOX are acute myelosupression and chronic cardio toxicity. While resulting stomatitis, nausea, vomiting, and hair loss are reversible, anthracycline-induced effects on cardiac tissue is cumulative, and the resulting cardiomyopathy can lead to congestive heart failure.

In addition to myelosupression and cardio toxicity, another concern is the development of drug resistance. While DOX-treated patients exhibit astonishing remission rates, the frequency of relapse can reach 50%, which is often due to the development of drug resistance. Mechanisms of resistance have been intensively studied and include alterations within topo II, and the over-expression of drug efflux pumps. Both mechanisms result in reduced drug/enzyme interaction. Natural and acquired anthracycline resistance is often due to over-expression of membrane-bound proteins belonging to the ABC carrier group. Such proteins are capable of rapidly pumping out lipophilic drugs from cells and reducing their effective intracellular concentrations. The most common overly expressed efflux pumps are the P-glycoprotein and the MRP protein. Since these pumps are capable of operating on a great variety of amphiphilic cytotoxic drugs, DOX-resistant cells generally exhibit a multi-drug resistance phenotype.

One approach to dealing with DOX-induced side effects is to administer additional drugs that specifically ameliorate those effects. In that respect, DOX is often prescribed along with dexrazoxane, which functions as a cardio-protective agent. P-glycoprotein-mediated resistance can be reduced by a variety of certain chemicals that inhibit this pump, however, their clinical use has yet to prove effective.

As discussed above, one approach to DOX side effects and resistance is the development of additional drugs that reduce these associated conditions. As an alternative approach, intense research has progressed in the development of anthracycline analogs that retain the DOX-mediated anti-neoplastic phenotype while reducing or eliminating its associated side effects. One such analog is annamycin (ANN). ANN has four structural differences compared to DOX, 1) removal of the amino group at the 3' position of the sugar and replacement by a hydroxyl group; 2) demethoxylation at position 4 of the aglycone; 3) addition of iodine at position 2', with axial orientation; and 4) inversion (epimerization) of the hydroxyl group at position 4'. These changes were chosen with the following rationale. Alteration I had been shown to confer partial lack of cross-resistance while at the same time failing to alter the ability to inhibit topo II; in addition, this change was believed to reduce cardio toxicity. Alterations 2 and 3 were believed to increase the lipophilic nature of the molecule. The rationale for such a change was the belief that this would affect cellular uptake and retention; in addition, it would also permit liposomal delivery, which had been shown to increase activity and decrease cardio toxicity with another anthracyline, daunorubicin. Alteration 4 was believed to reduce cardio toxicity.

Despite the differences between ANN and DOX, ANN retained an ability to stimulate cancer cell death, apparently by inhibiting topoisomerase II. Importantly, ANN exhibited a lack of cross resistance (i.e.: DOX-resistant cells remain sensitive to ANN). The mechanism for this lack of cross resistance appears to be the high affinity ANN has for lipid membranes. This affinity results in increased cellular uptake and increased cellular retention. ANN efflux may not be related to P-glycoprotein. Altered cellular distribution has also been observed; ANN exhibits perinuclear localization, as compared with DOX, which accumulates in the nucleus. In addition, ANN has been shown to be less cardiotoxic in mouse studies. Due to the extremely lipophilic nature of ANN, it must be administered within a liposomal carrier.

The perinuclear nature of ANN may render it less suitable as a compound to deliver the Auger electrons. Without reaching to the DNA duplex, the short range of Augers, even at $10^6$ Gy, are really not effective anywhere else in the cytoplasm.

In addition to ANN, iododeoxyuridine, a halogenated pyrimidine which competes with thymidine in the synthesis of DNA is a potential candidate. As to the latter, halogenated pyrimidine-substituted DNA is more sensitive to ionizing radiation due to the generation of reactive intermediates and inhibition of DNA repair. In this model the proximity of the iodine to DNA will permit the extremely high dose of released Auger electrons to induce non-repairable double stranded breaks and tumor cell death. Again, the same advantages of limiting radiation with mono-energetic beams to tumor tissues containing the iodinated anti-cancer agent will avoid systemic toxicity, and further, the dosage of the anti-cancer drug will be lower assuming cell killing will be due mainly to the in situ radiation effect. Note that the radioactive I-125 (decays by its K-electron being captured by the nucleus) can also deliver the massive Auger dose at small distance and $^{125}$I-dU would cause the well known double strand breaks in the DNA. But such a damage to the DNA is systemic. It would be highly toxic to the bone marrow, for example, and therefore, it is precisely the kind of collateral damages that the present method seeks to avoid.

Ruthenium based organometallic compounds have been extensively tested for their role as chemotherapeutic agents. Many of these agents have been shown to have an effect through DNA binding, usually detected by effects on DNA synthesis, induction of the SOS (error prone) repair response and reduction of RNA synthesis. For amine and imine complexes of ruthenium such as cis-$[_{Cl2}(NH_3)_4Ru^{III}]Cl_2$ and $(Him)[trans[(Im)_2Cl_4Ru^{III}]$ a direct correlation between cytotoxicity and DNA binding has been observed. Binding to both single- and double-stranded DNA occurs preferentially at G but also occurs at A and C. EDTA complexes of $Ru^{III}$ and $Ru^{IV}$ have also shown anti-cancer activity, apparently through DNA binding.

Monoacido forms such as $[CH_3CH_2CO_2(NH_3)_5Ru](ClO_4)_2$ can be active but multichloro forms show the best anti-tumor activity. In some cases best activity has to be traded off against solubility.

Many molecules of the general formula $Cl_3LRu$ where L is one or more organic groups derived from pyridine, phenanthroline, quinoline, imidazol, indazole etc., show extensive anti-cancer activity with variable levels of general cell cytotoxicity. For most of these, an activity mediated through DNA binding has been implicated.

The ruthenium complexes with polyaminopolycarboxyl chelating ligands are six-coordinated, octahedral and highly water soluble. In at least some cases, their antitumor activity has been shown to be possibly by cross-linking guanines on DNA. That they intercalate into DNA is suggested by their ability to change the conformation of plasmid DNA and block DNA recognition and restriction-enzyme cleavage in vitro. Some of these, such as [(edta)-Ru$^{II}$]—are rapidly air oxidized; their activity may depend on the Ru$^{III}$ form being activated by reduction in hypoxic tumors.

The final major group of important ruthenium compounds is the dimethyl sulfoxide complex group. They exhibit antitumor activity and are relatively nontoxic with LD$_{50}$'s up to ~1 g/kg. For at least some of these there has been extensive work done on their interaction with DNA with, for example, NMR evidence showing a fairly stable macrocyclic chelate with d(GpG). The cis-form of [Cl$_2$(Me$_2$SO)$_4$Ru] does not significantly affect the conformation of B-DNA and increases its thermal stability while the trans-form binds more rapidly, making significant alterations to the CD spectrum of the DNA and possibly promoting B to Z transitions in regions of appropriate nucleotide sequence. The imidazol derivative of the dimethylsulfoxide complex (NAMI) shows low general cellular toxicity and good antitumor activity, but its activity appears to be completely unrelated to its ability to bind DNA.

It is clear that many ruthenium compounds will enter living cells and become bound to the nuclear DNA where they may cause disruption of DNA synthesis and/or related processes. Those molecules showing lower levels of antitumor activity probably reflect reduced levels of cellular access and/or reduced levels of binding. Binding to DNA by these molecules is often a form of insertion between stacked base pairs or intercalation into one of the grooves. As such, given a stacking distance of 3.4 Å, the ruthenium is likely to be held in intimate contact with sensitive regions of the double helix. Production of Auger electrons from such ruthenium atoms will amplify the destructive effect of the molecules allowing lower, safer dosages to be used while maximizing the antitumor effect.

The phenanthroline groups on Dichlorotris(1,10-phenanthroline) ruthenium (II) hydrate absorb in the UV region with a peak absorbance at or near 260 nm. Loss or damage to these groups can be estimated by determining the UV absorbance before and after treatment with X-rays generated by a silver target which is optimum for Ru. Over several experiments replicating treatments with 100 Rad or using increasing amounts of X-rays between 50 Rads and 1000 Rads a loss of UV absorbance at 260 nm of 0.5% to 1% per 100 Rads has been determined. Where the Ruthenium compound is used at a concentration of 20 µg/ml and given the fresh weight of the dye of 712.61 g, this indicates that of the order of $10^{14}$ phenanthroline groups are damaged per ml. Since it can be assumed that not all Auger electron release will result in damage to a dye molecule, this indicates that a minimum of $10^{14}$ events per ml take place per 100 Rads X-rays delivered.

Platinum complexes such as cisplatin (cis-diamminedichloroplatinum) are known antineoplastic agents. Cisplatin is toxic, but by means of production of Auger electrons from platinum atoms in accordance with the method of the invention, the antineoplastic effect can be increased. This would permit use of the agent in lower dosages, thereby reducing collateral damage.

DNA binding compounds and complexes with metal elements which potentially are useful in the present invention are described in the aforementioned U.S. Pat. No. 6,224,848 the disclosure of which is incorporated herein by reference.

The invention claimed is:

1. A method for preferential disruption of malfunctioning cells in a living mammal, which comprises:
    (a) administering a compound which associates with DNA in cells of said mammal, said compound comprising a pre-selected element selected from the group consisting of Pt, Ca, Ti, Br, I, Gd, Y and Ru; and then
    (b) irradiating a selected region, in which malfunctioning cells having said compound associated with DNA are located, with line emission x-rays from an X-ray tube, said line emission X-rays being of an energy selected to cause emission of Auger electrons from said pre-selected element of said compound in a dose effective to disrupt DNA proximate to the irradiated pre-selected element, said dose for each activation of said X-ray tube being at least about $10^6$ Gy localized with a distance of a few atomic diameters from the pre-selected element, said selected region being a localized region which predominantly contains the malfunctioning cells so as to localize the effects of disrupting DNA to the malfunctioning cells and to minimize the effect on normal cells.

2. A method according to claim 1, wherein the compound intercalates into the DNA helix.

3. A method according to claim 1, wherein the compound binds to the DNA.

4. A method according to claim 1, wherein the compound is substantially non-toxic.

5. A method according to claim 1, wherein the compound has an affinity for both normal and malfunctioning cells.

6. A method according to claim 5, wherein the compound is substantially non-toxic.

7. A method according to claim 1, wherein the compound has a selective affinity for malfunctioning cells.

8. A method according to claim 1, wherein the compound is selected from the group consisting of annamycin, bromodeoxyuridine, bromodeoxycytosine and iododeoxyuridine 9. A method according to claim 1, wherein the compound is iododeoxyuridine.

10. A method according to claim 9, wherein the compound is bromodeoxyuridine.

11. A method according to claim 1, wherein the compound is a ruthenium compound which binds to or intercalates into DNA.

12. A method according to claim 1, wherein the compound is cisplatin.

13. A method according to claim 1, wherein the pre-selected element of the compound is selected from the group consisting of Ru, I and Gd.

14. A method according to claim 1, wherein the malfunctioning cells of the mammal's body are superficial and the pre-selected element of the compound is Br.

15. A method according to claim 1, wherein the compound is selected to have a high rate of excretion by normal physiological processes.

16. A method according to claim 1, wherein the compound is selected for stability against dissociation of the pre-selected element during the time prior to excretion or metabolism of the compound.

17. A method according to claim 1, wherein an end window transmission x-ray tube producing bright line emission x-rays is used for irradiating.

18. A method according to claim 17, wherein an e-beam generated in the x-ray tube is focused on a thin target having a thickness selected to provide the line emission x-rays, said thickness not exceeding about 40 μm, said target being inside the tube and functions as part of the end window.

19. A method according to claim 18, wherein the target and the e-beam energy are selected to provide monochromatic line emission x-rays having an energy above and sufficiently near the K-absorption edge of the pre-selected element of the compound to cause said emission of Auger electrons.

20. A method according to claim 19, wherein the thin target is selected from the group consisting of Mo, Ag, La, Sr and Tm.

21. A method according to claim 18, wherein the target and the e-beam energy are selected to provide monochromatic line emission x-rays having an energy above and sufficiently near the L-absorption edge of the pre-selected element of the compound to cause said emission of Auger electrons.

22. A method according to claim 21, wherein the thin target is Rb.

23. A method according to claim 22, wherein the pre-selected element of the compound is Pt.

24. A method according to claim 1, wherein the dose of at least about $10^6$ Gy is released within a distance from the element of the compound of up to about 10 angstroms.

25. A method according to claim 1, wherein step (b) is repeated at least once.

26. A method according to claim 25, wherein Auger electrons are released during each repetition of step(b) with a dose of at least about $10^6$Gy.

27. A method according to claim 26, wherein the dose of at least about $10^6$ Gy is released within a distance from the element of the compound of up to about 10 angstroms.

28. A method according to claim 1, wherein step (b) is performed on cells removed from the mammal.

29. A method according to claim 28, wherein after step (b) is performed, the removed cells are returned to the mammal.

30. A method according to claim 28, wherein after step (b) is performed, the removed cells are transplanted.

31. A method according to claim 1, wherein step (a) and step (b) are performed on cells removed from the mammal.

32. A method according to claim 31, wherein after step (b) is performed, the removed cells are returned to the mammal.

33. A method according to claim 31, wherein after step (b) is performed, the removed cells are transplanted.

34. A method according to claim 1, wherein the malfunctioning cells are tumor or cancer cells and the mammal is a human.

35. A method according to claim 34, wherein the compound intercalates into the DNA helix.

36. A method according to claim 34, wherein the compound binds to the DNA.

37. A method according to claim 34, wherein the compound is substantially non-toxic.

38. A method according to claim 34, wherein the compound has an affinity for both normal and cancerous cells.

39. A method according to claim 38, wherein the compound is substantially non-toxic.

40. A method according to claim 34, wherein the compound has a selective affinity for cancerous cells.

41. A method according to claim 34, wherein the compound is selected from the group consisting of annamycin, bromodeoxyuridine, bromodeoxycytosine and iododeoxyuridine.

42. A method according to claim 34, wherein the compound is iododeoxyuridine.

43. A method according to claim 34, wherein the compound is bromodeoxyuridine.

44. A method according to claim 34, wherein the compound is a ruthenium compound which binds to or intercalates into DNA.

45. A method according to claim 34, wherein the compound is Cisplatin.

46. A method according to claim 1, wherein the pre-selected element of the compound is selected from the group consisting of Ru, I and Gd.

47. A method according to claim 1, wherein the cancerous cells of the human's body are superficial and the pre-selected element of the compound is Br.

48. A method according to claim 34, wherein the compound is selected to have a high rate of excretion by normal physiological processes.

49. A method according to claim 34, wherein the compound is selected for stability against dissociation of the pre-selected element during the time prior to excretion or metabolism of the compound.

50. A method according to claim 34, wherein an end window transmission x-ray tube producing bright line emission x-rays is used for irradiating.

51. A method according to claim 50, wherein an e-beam generated in the x-ray tube is focused on a thin target having a thickness selected to provide the line emission x-rays, said thickness not exceeding about 40 μm, said target being inside the tube and functions as part of the end window.

52. A method according to claim 51, wherein the target and the e-beam energy are selected to provide monochromatic line emission x-rays having an energy above and sufficiently near the K-absorption edge of the element of the compound to cause said emission of Auger electrons.

53. A method according to claim 52, wherein the thin target is selected from the group consisting of Mo, Ag, La, Sr and Tm.

54. A method according to claim 51, wherein the target and the e-beam energy are selected to provide monochromatic line emission x-rays having an energy above and sufficiently near the L-absorption edge of the pre-selected element of the compound to cause said emission of super electrons.

55. A method according to claim 54, wherein the thin target is Rb.

56. A method according to claim 55, wherein the pre-selected element of the compound is Pt.

57. A method according to claim 34, wherein the dose of at least about $10^6$ Gy is released within a distance from the element of the compound of up to about 10 angstroms.

58. A method according to claim 34, wherein step (b) is repeated at least once.

59. A method according to claim 58, wherein Auger electrons are released during each repetition of step (b) with a dose of at least about $10^6$ Gy.

60. A method according to claim 59, wherein the dose of at least about $10^6$ Gy is released within a distance from the element of the compound of up to about 10 angstroms.

61. A method according to claim 1, wherein the malfunctioning cells are cancerous cells and the mammal is a human, wherein the method comprises:
   (a) administering to the human the compound which associates with DNA, in cells of said human, said compound comprising a pre-selected element selected from the group consisting of Br, Ru, I, Gd and Pt; and then
   (b) irradiating at least once, by means of an end window transmission x-ray tube, the selected region, in which the cancerous cells having said compound associated with DNA are located, with line emission x-rays of an energy selected to cause emission of Auger electrons from said pre-selected element of said compound in a dose effective to disrupt DNA proximate to the irradiated pre-selected element, said dose for each activation of said x-ray tube being at least about $10^6$ Gy within a distance from the pre-selected element of the compound of up to about 10 angstroms.

62. A method according to claim 61, wherein the compound intercalates into the DNA helix.

63. A method according to claim 61, wherein the compound binds to the DNA.

64. A method according to claim 61, wherein the compound is substantially non-toxic.

65. A method according to claim 61, wherein the compound has an affinity for both normal and tumorous cells.

66. A method according to claim 65, wherein the compound is substantially non-toxic.

67. A method according to claim 61, wherein the compound has a selective affinity for tumorous cells.

68. A method according to claim 61, wherein the compound is selected from the group consisting of annamycin, bromodeoxyuridine, bromodeoxycytosine and iododeoxyuridine.

69. A method according to claim 61, wherein the compound is iododeoxyuridine.

70. A method according to claim 61, wherein the compound is bromodeoxyuridine.

71. A method according to claim 61, wherein the compound is a ruthenium compound which binds to or intercalates into DNA.

72. A method according to claim 61, wherein the compound is cisplatin.

73. A method according to claim 61, wherein the compound is selected to have a high rate of excretion by normal physiological processes.

74. A method according to claim 61, wherein the compound is selected from stability against dissociation of the pre-selected element time prior to excretion or metabolism of the compound.

75. A method according to claim 61, wherein an e-beam generated in the x-ray tube is focused on a thin target having a thickness selected to provide the line emission x-rays, said thickness not exceeding about 40 μm, said target being inside the tube and functions as part of the end window.

76. A method according to claim 75, wherein the target and the e-beam energy are selected to provide monochromatic line emission x-rays having an energy above and sufficiently near the K-absorption edge of the pre-selected element of the compound to cause said emission of Auger electrons.

77. A method according to claim 76, wherein the thin target is selected from the group consisting of Sr, Ag, La, and Tm.

78. A method according to claim 75, wherein the target and the e-beam energy are selected to provide monochromatic line emission x-rays having an energy above and sufficiently near the L-absorption edge of the pre-selected element of the compound to cause said emission of Auger electrons.

79. A method according to claim 78, wherein the thin target is Rb.

80. A method according to claim 79, wherein the pre-selected element of the compound is Pt.

81. A method for treating malfunctioning cells in a living mammal, which comprises:
(a) providing a kit comprising
(1) an x-ray tube having a target comprising a selected metal, said tube being capable of emitting monochromatic line emission x-rays; and (2) a compound comprising a selected element selected from the group consisting of Pt, Ca, Ti, Br, I, Gd, Y and Ru, said compound being capable, upon administration to said mammal, of associating with DNA in cells of said mammal; the selected metal of said target and the selected element of said compound being selected together:
(i) for said metal of said target to emit line emission x-rays having an energy above and near the K-absorption edge or the L-absorption edge of the selected element of said compound, and
(ii) for said element of said compound to release a dose of Auger electrons upon irradiation by said line emission x-rays in a dose effective to disrupt DNA proximate to the irradiated selected element, said dose for each activation of said X-ray tube being at least about $10^6$ Gy localized with a distance of a few atomic diameters from the pre-selected element;
(b) administering the compound to the mammal and
(c) irradiating a selected region, in which malfunctioning cells having said compound associated with DNA are located, with the monochromatic line emission x-rays form the x-ray tube to cause emission of Anger electrons from said pre-selected element of said compound in the dose effective to disrupt DNA proximate to the irradiated pre-selected element.

82. A method according to claim 81, wherein said x-ray tube is an end window transmission x-ray tube capable of emitting bright, line emission x-rays, said x-ray tube comprising an evacuated, elongated chamber having first and second ends, the first end being connected to a power supply, and within said chamber: electron emitter means near the first end for generating a beam of electrons; an end window transparent to x-rays at the second end, an inner portion of said end window comprising said target; and means for focusing said electron beam on said target.

83. A method according to claim 82, wherein the target has a thickness selected to provide the line emission x-rays, said thickness not exceeding about 40 μm.

84. A method according to claim 81, wherein the target is selected from the group consisting of Rb, Mo, Ag, La, Sr and Tm.

85. A method according to claim 81, wherein the compound is substantially non-toxic.

86. A method according to claim 81, wherein the compound has an affinity for both normal and malfunctioning cells.

87. A method according to claim 86, wherein the compound is substantially non-toxic.

88. A method according to claim 81, wherein the compound has a selective affinity for malfunctioning cells.

89. A method according to claim 81, wherein the compound is selected from the group consisting of annamycin, bromodeoxyuridine, bromodeoxycytosine and iododeoxyuridine.

90. A method according to claim 81, wherein the compound is iododeoxyuridine.

91. A method according to claim 81, wherein the compound is bromodeoxyuridine.

92. A method according to claim 81, wherein the compound is a ruthenium compound which binds to or intercalates into DNA.

93. A method according to claim 81, wherein the compound is cisplatin.

94. A method according to claim 81, wherein the pre-selected element of the compound is selected from the group consisting of Br, Ru, I, Gd and Pt.

* * * * *